United States Patent [19]
Messerschmidt

[11] Patent Number: 5,859,434
[45] Date of Patent: Jan. 12, 1999

[54] INFRARED SPECTROSCOPIC SAMPLING ACCESSORY HAVING A REMOTELY MOUNTED CRYSTAL PLATE

[75] Inventor: Robert G. Messerschmidt, Albuquerque, N. Mex.

[73] Assignee: CIC Photonics, Inc., Albuquerque, N. Mex.

[21] Appl. No.: 897,228

[22] Filed: Jul. 21, 1997

Related U.S. Application Data

[63] Continuation of Ser. No. 767,441, Dec. 16, 1996, abandoned, which is a continuation of Ser. No. 425,252, Apr. 17, 1995, abandoned, which is a continuation of Ser. No. 292,969, Aug. 22, 1994, abandoned, which is a continuation of Ser. No. 19,377, Feb. 18, 1993, abandoned.

[51] Int. Cl.$^6$ .................................................. G01N 21/35
[52] U.S. Cl. ................................. 250/339.11; 250/341.8
[58] Field of Search ............................... 250/339, 341.3, 250/341.8, 339.11

[56] References Cited

U.S. PATENT DOCUMENTS

| | | |
|---|---|---|
| 3,177,759 | 4/1965 | Wilks, Jr. .................................. 356/51 |
| 3,279,307 | 10/1966 | Wilks, Jr. . |
| 4,602,869 | 7/1986 | Harrick . |
| 5,153,675 | 10/1992 | Beauchaine .............................. 356/346 |
| 5,214,286 | 5/1993 | Milosevic et al. ....................... 250/339 |

FOREIGN PATENT DOCUMENTS 2228083  8/1990  United Kingdom .

Primary Examiner—Constantine Hannaher
Attorney, Agent, or Firm—Antton & Associates P.C.

[57] ABSTRACT

A system for delivering infrared energy to a sample using frustrated internal reflectance in which a crystal for receiving the infrared energy is formed integrally with a removable mounting card. The mounting card is removable so that new samples can be sampled by quickly replacing the crystal with a new crystal having a new sample for analysis. Preferably, the crystal has the shape of a Fresnel lens. The infrared energy can be delivered to the crystal so that it experiences a single internal reflection and mounted in a card to form a surface that is integral with one side of the card to facilitate rapid cleaning and reuse of the card.

8 Claims, 4 Drawing Sheets

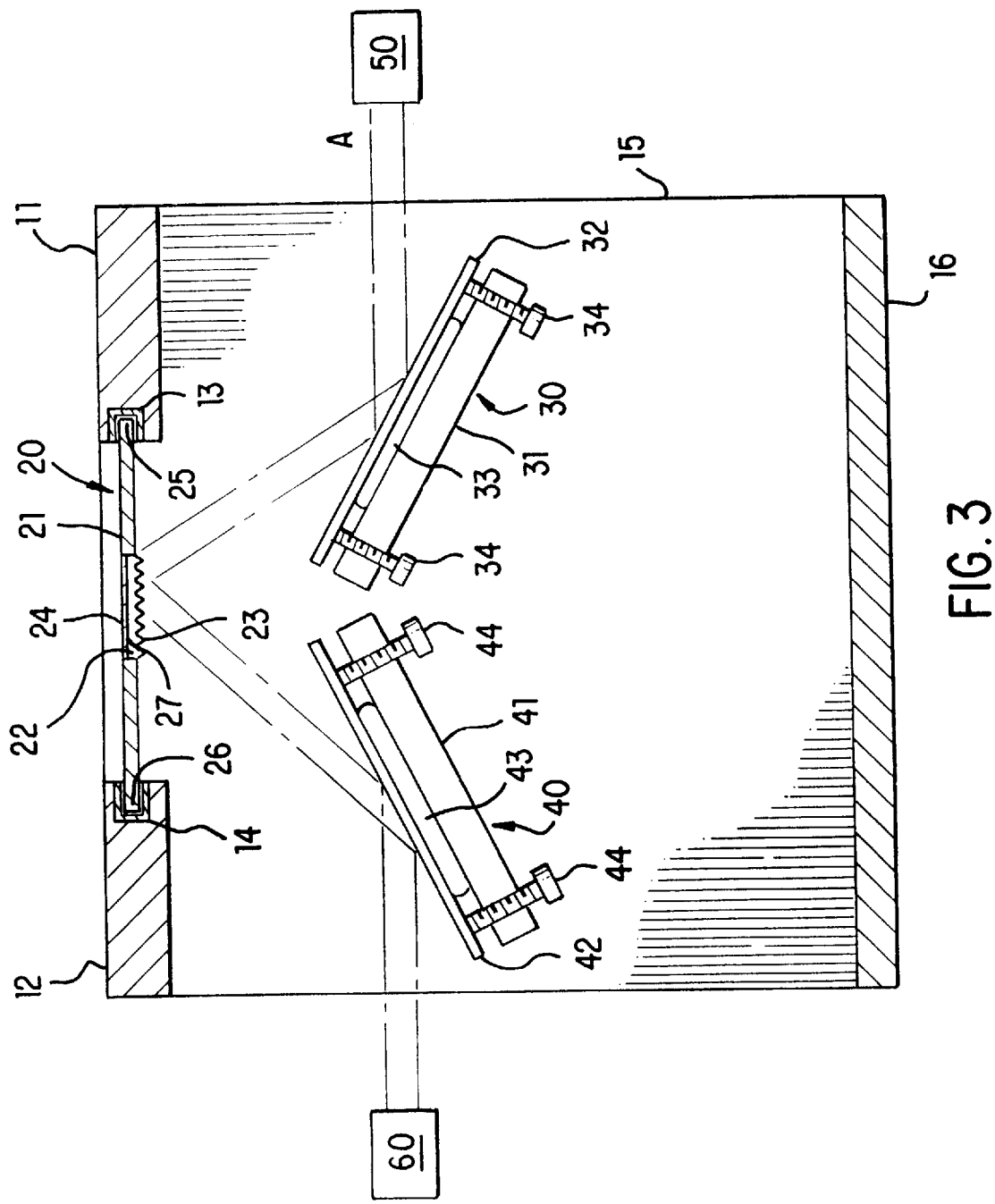

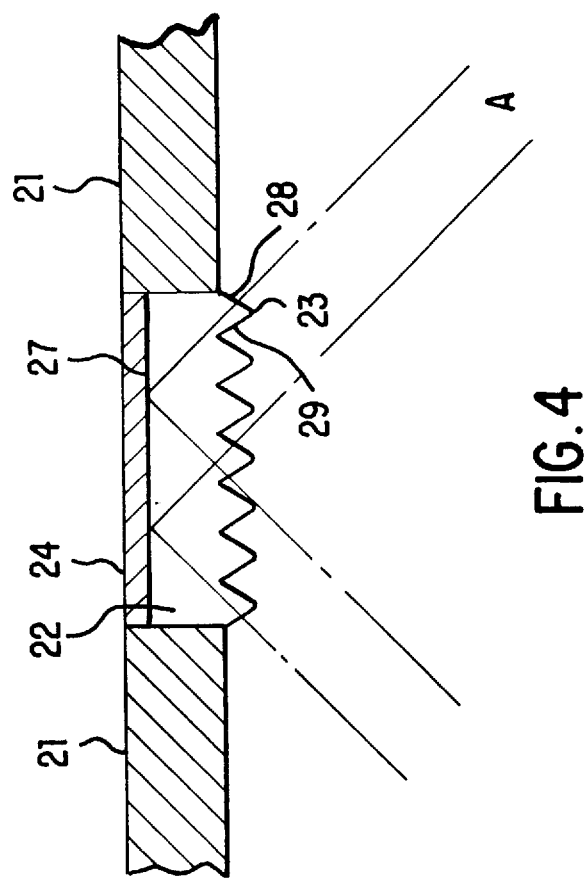

5,859,434

INFRARED SPECTROSCOPIC SAMPLING ACCESSORY HAVING A REMOTELY MOUNTED CRYSTAL PLATE

This application is a continuation of application Ser. No. 08/767,441, filed Dec. 16, 1996, (abandoned) which was a continuation of application Ser. No. 08/425,252, filed Apr. 17, 1995, (abandoned) which was a continuation application of Ser. No. 08/292,969, filed Aug. 22, 1994, (abandoned) which was a continuation application of parent application Ser. No. 08/019,377, filed Feb. 18, 1993 (abandoned).

BACKGROUND AND SUMMARY OF THE INVENTION

It is known that a crystal material such as AMTIR-1, silver halide, silver bromide, KRS-5 or the like can be used to attain frustrated internal reflectance of infrared energy. The infrared radiant energy is injected into the crystal so as to reflect at more than the critical angle. The resulting internal reflectance establishes an evanescent field around the crystal. Material placed in or near contact with the crystal will couple with the evanescent field generated by the frustrated internal reflection. A material having spectral absorption features in the bandwidth of the infrared energy imparts a spectral signature to the infrared energy undergoing frustrated internal reflection by coupling with the evanescent field. Ejecting the infrared energy from the crystal to an infrared detector permits the acquired spectrum to be measured using, for example, a known FT-IR spectrometer such as a Mattson Galaxy 5000.

The issue remains how best to deliver the infrared energy to a sample so that it can experience evanescent field coupling with the material being spectroscopically analyzed. Various elaborate proposals have been advanced. For example, U.S. Pat. No. 4,602,869 to Harrick proposes mounting two mirrors on an arm so as to reflect the infrared energy into a prism. The infrared radiant energy can experience between one and three internal reflections which lead to the infrared energy acquiring the spectral content of the material under analysis. The internal reflection prism cell disclosed by Harrick, however, is quite elaborate in its mechanical construction which adds to the cost of the unit while simultaneously detracting from its ease of use. There is no simple way contemplated for removing the crystal or for moving onto additional measurements. Nevertheless, the solution proposed by Harrick has proven to be one of the more successful spectroscopic accessories on the market due, in part, to its simplicity relative to other comparable accessories.

Another proposal is that presented in U.K. Patent Application GB 2 228 083 in which a crystal is mounted and sealed to a fluid chamber so as to become a part of the wall of the chamber while also contacting the fluid. The infrared energy experiences multiple internal reflections. Forming the crystal integral with the fluid containment vessel has an inherent advantage of simplicity of use in that the spectra of new liquids can be attained simply by emptying the vessel, cleaning the inner face of the crystal and refilling it with the new specimen. The requirement for multiple internal reflections also requires the crystal to be rather large which complicates the construction of the fluid chamber. The concept of this fluid chamber has enjoyed no known commercial acceptance or success.

U.S. Pat. No. 3,177,759 to Wilks, Jr. discloses a particularly simple and powerful geometry for a crystal that achieves frustrated internal reflection. The crystal has a series of ridges in the form of triangular prisms which are aligned in a common direction to form what amounts to a Fresnel lens. Infrared radiant energy enters the crystal through a first face of any of the ridges, experiences a single internal reflection and then exits through a second face of any of the ridges. The resulting prism has minimum weight and can be formed through simple injection molding. This crystal, however, is not mounted in any particular base such that the mechanical complexity of the accessory is not reduced.

There is a need in the art for a simple, efficient and mechanically simplified way to deliver infrared energy to a sample so that it can experience evanescent field coupling with material that being spectroscopically analyzed. There is a need to avoid the mechanical complexity of having a plurality of internal reflections within the crystal while also being able to rapidly change between new samples. And there is a need to attain mechanical simplicity using an optical apparatus that is economical to fabricate.

The present invention meets these and other needs by combining a simple infrared crystal support assembly for delivering the infrared energy to an infrared crystal where it can experience frustrated internal reflectance in which the infrared crystal is formed integrally with a removable crystal mounting plate. The support assembly supports a removable crystal mounting plate so that new measurements can be made by quickly replacing the crystal mounting plate having one crystal with a new crystal mounting plane having another crystal for analysis of a different sample. Preferably, the crystal has the shape of a Fresnel lens of modest size that is easily fabricated. The infrared energy can be delivered to the crystal so that it experiences a single internal reflection which helps to reduce the complexity associated with crystals using a plurality of internal reflections. The crystal can be mounted in its crystal mounting plate to form a surface that is integral with one side of the crystal mounting plate to facilitate rapid cleaning and reuse of the crystal mounting plate.

The foregoing objectives, features and advantages of the present invention, and more, are explained in detail below.

BRIEF DESCRIPTION OF THE DRAWINGS

FIG. 3 is a section view taken along line III—III of FIG. 1.

FIG. 4 is an enlargement of a portion of FIG. 3, showing the infrared crystal.

DETAILED DESCRIPTION

Figure 1:
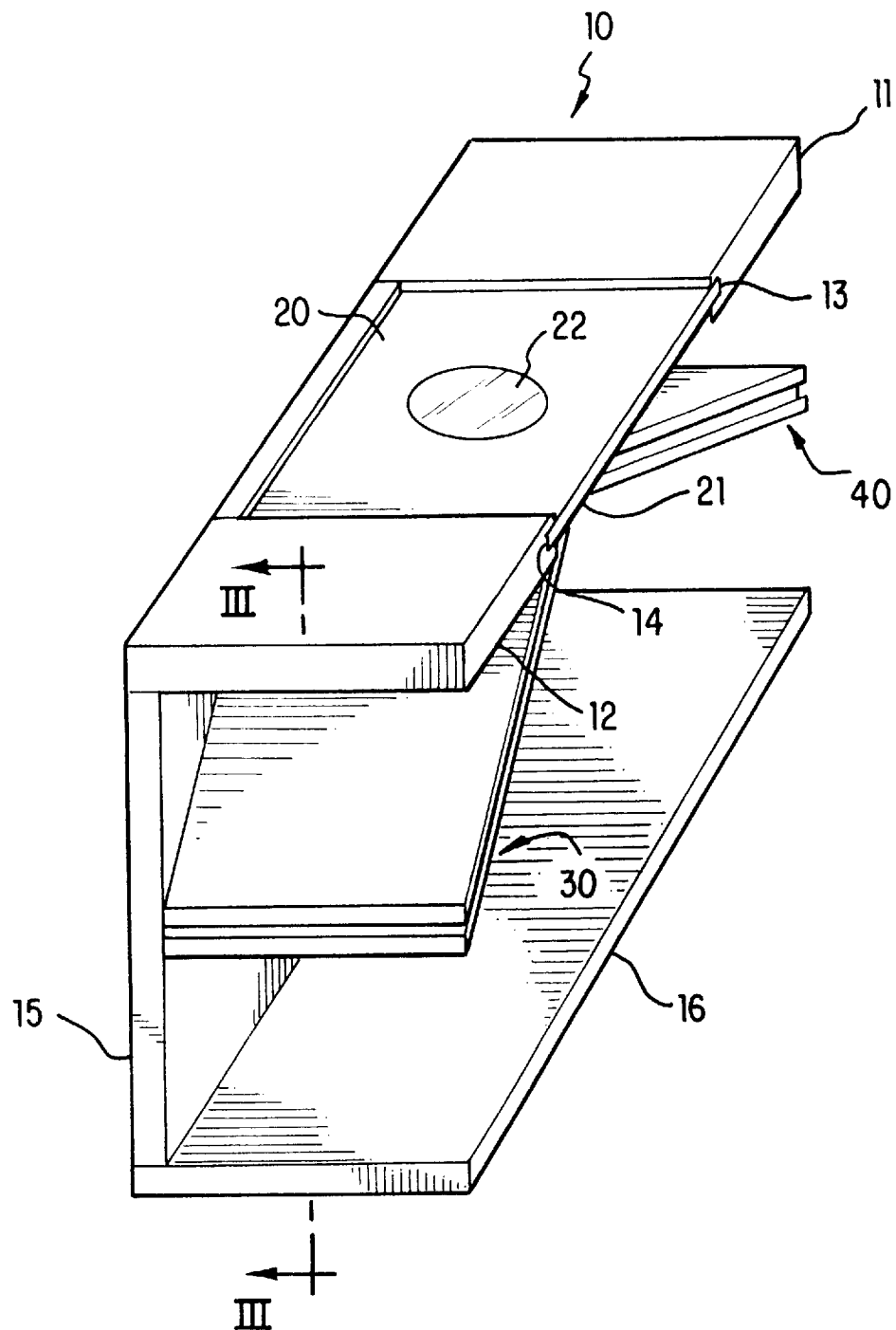
FIG. 1 is a perspective view of an infrared crystal support assembly according to a first embodiment of the present invention.

FIG. 1 shows an infrared crystal support assembly 10 according to the present invention. Infrared crystal support assembly 10 comprises a back 15 and a bottom 16. A first plate support 11 and a second plate support 12 are attached to the back 15 and support the crystal mount assembly 20 using a first mounting bracket 13 and a second mounting bracket 14. First mirror assembly 30 and second mirror assembly 40 are also attached to the back 15, and are centered underneath the crystal mount assembly 20. As will be discussed in detail later, first mirror assembly 30 and second mirror assembly 40 are positioned in such a manner as to reflect an incoming beam to the infrared crystal 22 and then from the infrared crystal 22 to a detector as will be described below.

Figure 2:
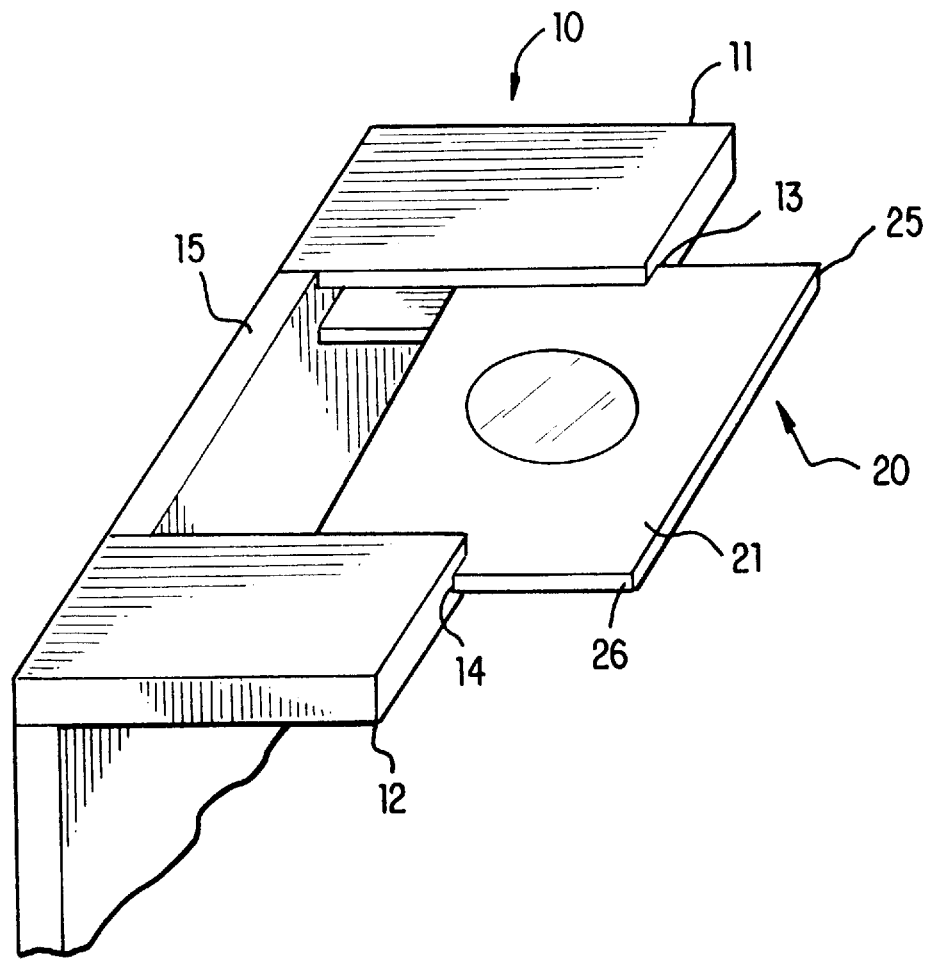
FIG. 2 is a partial perspective view of the infrared crystal support assembly showing the infrared crystal partially removed.

FIG. 2 shows a partial perspective view of the infrared crystal support assembly 10 and illustrates how the crystal mount assembly 20 may be removed and inserted. Crystal mount assembly 20 comprises crystal mounting plate 21 which has a first plate side 25 and a second plate side 26 opposed to one another. First plate support 11 and second plate support 12 have formed in them a first mounting bracket 13 and a second mounting bracket 14. First mounting bracket 13 and second mounting bracket 14 are sized and positioned so as to engage first plate end 25 and second plate end 26 so as to permit mounting plate 21 to slide in place. Crystal mount assembly 20 is easily mounted into and removed from the infrared crystal support assembly 10 by sliding first and second plate ends 25 and 26 within first and second mounting brackets 13 and 14, respectively.

FIG. 3 shows a section taken along line III—III of FIG. 1. The first mirror support 31 of the first mirror assembly 30 is affixed to back 15 of the infrared crystal support assembly 10. First mirror 32 is mounted to the first mirror support 31 by a resilient first mirror mounting pad 33. The orientation of first mirror 32 may be adjusted using four adjustment screws 34 which are positioned near the four corners of the mirror 32 and first mirror support 31. First mirror 32 is positioned so as to reflect an incoming beam from source 50 to the infrared crystal 22. Second mirror support 41 of the second mirror assembly 40 is also attached to back 15 of the infrared crystal support assembly 10. Second mirror 42 is mounted to the second mirror support 41 by a resilient first mirror mounting pad 43. The orientation of second mirror 42 may be adjusted using four adjustment screws 44 which are positioned near the corners of second mirror support 41 and second mirror 42. Second mirror 42 is oriented so as to receive a beam exiting the infrared crystal 22 and reflect it to an infrared detector 60 for analysis.

FIG. 4 shows an enlarged portion of FIG. 3. Infrared crystal 22 is mounted within the crystal mounting plate 21 of the crystal mount assembly 20. Infrared crystal 22 has a backside 27 on which a sample 24 is placed for analysis. Opposite to the backside 27 of the infrared crystal 22 are a plurality of ridges 23 each having a first ridge surface 28 and a second ridge surface 29. The ridges 23 are substantially parallel to one another and to the first plate end 25 and second plate end 26.

The path of beam A is shown schematically in FIGS. 3 and 4. Source 50 directs a beam to first mirror 32. First mirror 32 is positioned so as to reflect the incoming beam to the infrared crystal 22. The incoming beam strikes a plurality of first surfaces 28 of the ridges 23 at an angle less than the critical angle and thereby passes into crystal 22. The beam strikes back surface 27 at an angle greater than the critical angle and is internally reflected. Beam A thereby interacts with the sample 24 which is placed in contact with back surface 27 by evanescent field coupling of the radiant energy with the material under analysis. After reflecting off the back surface 27, the beam strikes a plurality of second ridge surfaces 29 of the ridges 23 at an angle less than the critical angle thereby passing out of the crystal. The beam strikes second mirror 42 which is positioned so as to reflect the beam to infrared detector 60 for analysis.

The infrared crystal support assembly shown in the figures can be used in the following ways. The crystal mounting plate 21 is inserted into the mounting brackets 13, 14. As illustrated, the crystal mounting plate 21 is slid into the mounting brackets, although other methods of insertion are also contemplated such as, for example, simply dropping the crystal mounting plate in place using appropriate mounting brackets, not shown. The sample 21 is then placed in contact with the infrared crystal 22. Pressure can be applied to the sample to insure good contact with the crystal using means, not shown, which are known in the art. Infrared energy from infrared source 50 can be applied to the infrared crystal 22 and the energy ejected can be sampled using infrared detector 60. A spectrum can be obtained using a variety of means which are known, for example, an interferometer of an FT-IR spectrometer. These steps can be performed in any practical order which may change depending on the sample being spectroscopically analyzed.

After obtaining the spectrum, the crystal mounting plate 21 can be removed by, for example, sliding it out of contact with the mounting brackets 13, 14. The sample 24 can be removed from contact with the crystal. The crystal mounting plate 21 can then be prepared for a new sample. Alternately, a different crystal mounting plate can be inserted and the process can be repeated. The crystal mounting plate 21 is most simple in construction and thus easily fabricated. It is therefore a simple matter to make multiple crystal mounting plates for quick and easy replacement in the crystal mount assembly 21.

The principles, preferred embodiments and modes of operation of the present invention have been set forth in the foregoing specification. The embodiment disclosed herein should be interpreted as illustrating the present invention and not as restricting it. The foregoing disclosure is not intended to limit the range of equivalent structure available to a person of ordinary skill in the art in any way, but rather to expand the range of equivalent structures in ways not previously thought of. Numerous variations and changes can be made to the foregoing illustrative embodiments without departing from the scope and spirit of the present invention as set forth in the appended claims.

What is claimed is:

1. A system for obtaining an infrared spectrum from a sample to be spectroscopically analyzed, comprising:

an infrared crystal having a first side for supporting a sample for analysis, and a second side opposite to the first side, a horizontal crystal mounting plate, the infrared crystal being mounted integrally in the crystal mounting plate between the first and second plate ends, and mounting the infrared crystal in a horizontal position, a crystal support assembly which removably mounts at least a first support plate to support the crystal mounting plate in the horizontal position without blocking the crystal mounting plate from being removed and inserted, a flat first transfer mirror that launches the infrared energy directly into the crystal at an angle which produces frustrated internal reflectance, and a flat second transfer mirror reflects infrared energy exiting the crystal directly to an infrared detector.

2. A system for obtaining a spectrum as in claim 1, wherein the infrared crystal comprises a Fresnel crystal.

3. A system for obtaining a spectrum as claimed in claim 2, wherein the Fresnel crystal comprises a plurality of parallel prismatic ridges each have a first prismatic surface and a second prismatic surface, the first prismatic surfaces being positioned to receive the transmitted infrared energy into the crystal, the first side of the crystal being positioned so as to internally reflect the incoming radiation, and the second prismatic surfaces being positioned so as to allow the reflected transmitted infrared energy to pass out of the crystal.

4. A system for obtaining a spectrum as in claim 1, wherein the first support plate comprises a first mounting bracket, and further comprising a second support plate having a second mounting bracket, the first and second plate ends removably mount to the first and second mounting brackets so that the crystal mounting plate can be slid into and from the crystal support assembly, and the crystal support plate is sized to slidably engage the first and second mounting brackets.

5. A system for obtaining a spectrum as claimed in claim 4, wherein the first transfer mirror is positioned beneath the crystal mounting plate to launch the infrared energy into the crystal at less than the critical angle, the first transfer mirror being mounted on a first transfer mirror assembly, a second transfer mirror is positioned beneath the crystal mounting plate so as to reflect infrared energy exiting the infrared crystal toward an infrared detector, the second transfer mirror being mounted on a second transfer mirror assembly, and the first and second transfer mirror assemblies comprise first and second mirror supports affixed to the crystal support assembly, at least one resilient second mirror mounting pad affixed to the first and second mirror supports in such a manner that the orientation that the first and second mirrors may be adjusted.

6. A method of spectroscopically analyzing a sample through evanescent field coupling with frustrated internal reflectance in an infrared crystal, comprising:

inserting a crystal support plate into at least one mounting bracket without the mounting bracket obstructing the insertion of the crystal support plate, the crystal support plate being formed integral with the infrared crystal so as to be inserted with the crystal support plate and to hold the support plate horizontal, contacting a sample with the infrared crystal, directing with a first flat mirror infrared energy from an infrared source directly into the infrared crystal to experience a frustrated internal reflection, directing with a second flat mirror the infrared energy from the infrared crystal directly to an infrared detector that can be used to produce an infrared spectrum, removing the crystal support plate and the infrared crystal from the mounting bracket without the mounting bracket obstructing the removal of the crystal support plate, and inserting another crystal support plate having another crystal into the mounting bracket without the mounting bracket obstructing the insertion of the crystal support plate.

7. A method of spectroscopically analyzing a sample as claimed in claim 6, wherein inserting the crystal support plate comprises sliding the support plate into the mounting bracket.

8. A system for obtaining an infrared spectrum from a sample to be spectroscopically analyzed, comprising:

an infrared Fresnel crystal having a first side for supporting a sample for analysis, and a second side opposite to the first side, the second side comprising a plurality of parallel prismatic ridges, each of which has a first prismatic surface and a second prismatic surface, the first prismatic surfaces being positioned to receive the transmitted infrared energy into the crystal, the first side of the crystal being positioned so as to internally reflect the incoming radiation, and the second prismatic surfaces being positioned so as to allow the reflected transmitted infrared energy to pass out of the crystal, a horizontal crystal mounting plate, the infrared crystal being mounted integrally in the horizontal crystal mounting plate, the horizontal crystal mounting plate mounting the infrared crystal in a horizontal position, a crystal support assembly having first and second support plates comprising first and second mounting brackets which removably mounts the horizontal crystal mounting plate in the horizontal position so as to be removed and inserted from the crystal support assembly, and further comprising a second support plate having a second mounting bracket, the horizontal crystal mounting plate engaging the first and second mounting brackets so that the horizontal crystal mounting plate can be removed from the crystal support assembly, a first flat mirror positioned beneath the horizontal crystal mounting plate to launch the infrared energy directly into the crystal at less than a critical angle to produce a single frustrated internal reflection of the infrared energy within the infrared crystal, a second flat mirror positioned beneath the horizontal crystal mounting plate so as to reflect infrared energy exiting the infrared crystal directly to an infrared detector, first and second mirror assemblies comprising the first and second mirrors mounted on first and second mirror supports, respectively, the first and second mirror supports affixed to the crystal support assembly, at least one resilient second mirror mounting pad affixed to the first and second mirror supports in such a manner that the orientation of the first and second mirrors may be adjusted.

\* \* \* \* \*